United States Patent [19]

Pesa et al.

[11] Patent Number: 4,517,400
[45] Date of Patent: May 14, 1985

[54] DECARBONYLATION OF N-BUTYRALDEHYDE USING ZEOLITE CATALYSTS

[76] Inventors: Frederick A. Pesa, 764 Circlewood Dr., Aurora, Ohio 44202; Marcus W. Blaskie, 19007 Chagrin Blvd., Shaker Heights, Ohio 44122; Joseph R. Fox, 32167 Hamilton Dr., Solon, Ohio 44139

[21] Appl. No.: 508,352

[22] Filed: Jun. 27, 1983

Related U.S. Application Data

[62] Division of Ser. No. 376,331, May 10, 1982, abandoned.

[51] Int. Cl.³ ................................................ C07C 1/00
[52] U.S. Cl. ..................................................... 585/638
[58] Field of Search ......................................... 585/638

[56] References Cited

U.S. PATENT DOCUMENTS

| | | | |
|---|---|---|---|
| 3,352,924 | 11/1967 | Gladrow et al. | 260/604 |
| 4,039,584 | 8/1977 | Falbe et al. | 585/638 |
| 4,260,841 | 4/1981 | Holland et al. | 585/638 |

OTHER PUBLICATIONS

Tsuji et al., JACS, 90:1, Jan. 3, 1968.

*Primary Examiner*—Curtis R. Davis
*Attorney, Agent, or Firm*—Debra L. Pawl; David J. Untener; Larry W. Evans

[57] ABSTRACT

A process is provided for decarbonylating aldehydes to olefins having one less carbon atom than the aldehydes, carbon oxide and hydrogen, by passing the aldehydes over a catalyst comprising a metal selected from the group consisting of palladium, platinum, rhodium, copper, silver, gold and zinc supported on or exchanged onto a support.

13 Claims, No Drawings

DECARBONYLATION OF N-BUTYRALDEHYDE USING ZEOLITE CATALYSTS

This is a division of application Ser. No. 376,331 filed May 10, 1982 and now abandoned.

BACKGROUND OF THE INVENTION

1. Field of the Invention

The present invention relates to a novel process for decarbonylating aldehydes and specifically n-aldehydes. More particularly, this invention relates to the decarbonylation of n-butyraldehyde to produce propylene, carbon monoxide and hydrogen, by passing the n-butyraldehyde over a catalyst comprising a metal selected from a group consisting of palladium, platinum, rhodium, copper, silver, gold and zinc supported on or exchanged onto a zeolite. Further, this invention also relates to the decarbonylation of n-aldehydes by passing the n-aldehydes over a catalyst comprising a metal selected from the group consisting of palladium, copper, silver, gold and zinc supported on silica.

2. Description of Art

The hydroformylation of olefinically unsaturated carbon compounds to produce aldehydes is well known. However, the hydroformylation of many of these compounds result in the production of mixtures of both isomeric forms of the aldehydes. For instance, when propylene is hydroformylated, a mixture of normal and isobutyraldehyde is obtained wherein the n-isomer is predominant. Present processes have not been totally satisfactory in providing an economical process for producing primarily the iso form of the aldehyde.

A novel solution for economically producing branched aldehydes and, more particularly, isobutyraldehyde is provided by the process of the present invention. After olefins are hydroformylated to obtain a mixture of normal and branched aldehydes, the n-aldehydes are either decarbonylated after separation from the branched aldehydes or are selectively decarbonylated from the reaction mixture of normal and branched aldehydes to produce predominantly olefins having one less carbon atom than the aldehydes, carbon monoxide and hydrogen. These decarbonylation products are then recycled through another hydroformylation process to produce additional aldehydes. Thus, the process of the present invention provides in part an economical and efficient technique for producing isoaldehydes, such as isobutyraldehyde, by selectively decarbonylating the n-aldehydes and recycling the resulting olefins to the hydroformylation reaction.

Numerous hydroformylation or carbonylation catalysts have been disclosed in the art. For example, U.S. Pat. No. 3,352,924 to Gladrow et al. discloses a carbonylation reaction using crystalline alumino-silicate zeolites containing rhodium and cobalt. U.S. Pat. No. 4,185,038 to Carlock discloses a hydroformylation catalyst comprising rhodium and iridium compounds covalently bound to inorganic oxide polymers such as silica gel, alumina, silica-titania, alumino-silicate and open-lattice clays.

Various decarbonylation catalysts have also been disclosed. For example, U.S. Pat. No. 3,578,423 to Falbe et al. discloses a process for catalytically splitting isobutyraldehyde to produce carbon monoxide and hydrogen in the presence of nickel containing catalysts. U.S. Pat. No. 4,039,584 to Falbe et al. discloses a process for catalytically cleaving isobutyraldehyde to form propylene, carbon monoxide and hydrogen over a supported rhodium and/or platinum catalyst. Other decarbonylation catalysts have been disclosed by U.S. Pat. No. 4,200,589 to Scharf and U.S. Pat. No. 4,262,157 to Hori et al., including catalysts containing mixtures of copper oxide, manganese oxide, zinc oxide and diazabicycloalkenes optionally in the presence of a simple copper salt.

Finally, the use of aluminosilicates, such as zeolites and molecular sieves, to achieve selectivity between a mixture of various compounds based on differences in molecular shapes or sizes is known. For example, U.S. Pat. No. 3,535,398 discloses the use of aluminosilicates for selectively conducting an organic chemical reaction. The process separates straight-chain polar compounds from mixtures of the same with straight-chain non-polar compounds as well as the separation of cis-isomers from trans-isomers.

SUMMARY OF THE INVENTION

According to this invention, an aldehyde is decarbonylated to an olefin having one less carbon atom than the aldehyde, carbon monoxide and hydrogen, by passing the aldehyde over a catalyst comprising a metal selected from the group consisting of palladium, platinum, rhodium, copper, silver, gold and zinc supported on a zeolite.

The metal zeolite catalysts also exhibit a high selectivity and activity for the decarbonylation of predominantly an n-aldehyde from a reaction mixture of an n-aldehyde and a branched aldehyde to produce mainly an olefin, carbon monoxide and hydrogen which can be recycled for the production of aldehydes.

In another embodiment of the present invention, an aldehyde is decarbonylated to an olefin having one less carbon atom than the aldehyde, carbon monoxide and hydrogen, by passing the aldehydes over a catalyst comprising palladium, copper, silver, gold and zinc supported on silica.

DETAILED DESCRIPTION OF THE INVENTION

The present invention provides a process for decarbonylating aldehydes. However, the invention also provides a process for selectively decarbonylating n-aldehydes from mixtures of n-aldehydes and branched aldehydes to produce a mixture of branched aldehydes, olefins having one less carbon atom than the aldehyde, carbon monoxide and hydrogen. Thus, mixtures of n-aldehydes and branched aldehydes can be separated prior to employing the present invention or mixtures can be employed without prior separation. The separation of n-aldehydes from branched aldehydes can occur by various means known in the art.

The aldehydes used here are acyclic monoaldehydes having 4 to 20 carbon atoms. Examples of suitable aldehydes include but are not limited to butyraldehyde, methyl butyraldehyde, valeraldehyde, methyl valeraldehyde, caproaldehyde, heptaldehyde, decaldehyde, and the like. Preferred are the $C_4$ to $C_6$ aldehydes such as butyraldehyde, valeraldehyde and caproaldehyde and most preferred is butyraldehyde.

The olefins produced in the process of this invention will have one less carbon atom than the aldehyde employed. For example, when butyraldehyde is decarbonylated, the product olefin will be propylene. It is important to recognize that the production of the corresponding alkane, propane in the case of butyraldehyde, is undesirable.

The decarbonylation of the normal form of the aldehyde is made possible by utilizing the particular catalyst system of the present invention. The catalyst of this invention is comprised of a metal supported on or exchanged onto a zeolite or supported on silica. The metal is selected from the group of palladium, platinum, rhodium, copper, silver, gold and zinc, with palladium being preferred. The amount of metal supported on or exchanged onto the zeolite support or supported on the silica can range from about 0.1 to about 10% by weight based on total weight of metal and support. Preferably, the percent metal will range from about 0.5 to about 8%, most preferably from about 0.7 to about 5% by weight.

The zeolites used in this invention include both the natural zeolites, such as analcite, chabazite, heulandite, natrolite, stilbite and thomsonite and artificial zeolites commercially prepared. Preferred are the commercially prepared type "A" and "Y" zeolites such as NaY, 5A, 4A, and 3A and most preferred are the type "Y" zeolites such as NaY.

The metals can be either impregnated or exchanged on the zeolite support by conventional means. Impregnation can be accomplished by any of the well known techniques for depositing the metal into the pores of a support. Typically, the catalyst can be prepared by dissolving the metal in the form of an organic or inorganic salt such as nitrate, acetate or carbonate in a solvent such as water or acetone and contacting the zeolite with the solvent. The support is then dried and calcined. Preferably, the catalyst is exposed to a reducing atmosphere after calcination where it is believed that the metal salts are partially reduced to metallic form although some of the metals may remain in the oxidized form.

The metals can also be exchanged onto the zeolite by well known techniques. Typical ion exchange techniques include contacting the zeolite with a salt of the desired replacing metal cation or cations. Although a wide range of organic and inorganic salts can be employed, preference is given to chlorides, nitrates and sulfates.

The metals are also supported on silica. The silica supports used in this invention are the conventional silica supports known to those skilled in the art and commercially available. Typically, the silica supports have a surface area of about 5 to about 500 m$^2$/g. The metals are also impregnated on the silica supports by conventional means such as the technique used above for the zeolite catalyst.

Although not intending to be bound to theory, it is believed that the catalysts achieve, to a partial extent, their selectivity for reacting with predominantly the n-aldehydes based on differences in molecular shape or size of the n-aldehydes as compared to the branched aldehydes. The zeolite support may effect a physical separation of aldehydes which differ in molecular dimensions. For example, the straight chain aldehydes might be absorbed into or absorbed onto the zeolite structure to the exclusion of the bulkier branched chain aldehydes. Surprisingly, however, when the zeolites are used in combination with the above metals, not only is the selectivity of the reaction for decarbonylating n-aldehydes increased, but the selectivity for producing the desired products is increased. For example, the decarbonylation of butyraldehyde can yield propylene, propane, carbon oxides, hydrogen, water and other condensation products. However, the inventive catalyst is highly selective in decarbonylating predominantly n-butyraldehyde and in producing predominantly propylene, carbon monoxide and hydrogen. It is one of the objects of the invention to form olefins which are suitable recycle reactants for the hydroformylation reaction to produce the desired isoaldehyde, rather than forming alkanes which are unsuitable for recycling to the hydroformylation reaction.

The process conditions of the decarbonylation reaction can vary widely. Typically, the temperature may range from about 50° to about 500° C., preferably from about 100° to about 300° C. and most preferably from about 125° to about 250° C. Subatmospheric, atmospheric or superatmospheric pressure can be used, but typically the pressure ranges from about 1 to about 1,500 psig, preferably from about 5 to about 50 psig and most preferably at about atmospheric pressure. Typically, a diluent gas such as argon, krypton, helium, carbon dioxide or nitrogen can be employed. Preferably, conditions are chosen which will cause the reaction to occur in a vapor phase. The products are separated and recovered by methods known in the art.

SPECIFIC EMBODIMENTS

Example 1

Catalyst Preparation

Pd(CH$_3$COO)$_2$ (0.72 gms.) was mixed with 20 ml. of acetone and warmed on a hotplate until all of the Pd-acetate was dissolved. Approximately 13 ml. of the acetone-Pd-acetate solution was impregnated onto 11 gms. of NaY zeolite support (from Strem Chemicals). The support was then placed in a 125° C. oven to dry and more acetone was added to the acetone-Pd-acetate mixture, bringing its volume back to 20 ml. After the support had dried (approximately 0.5 hours) and cooled, the impregnation was repeated until all of the Pd-acetate had dissolved in the acetone and all of the acetone-Pd-acetate mixture had been taken up by the NaY support. The final catalyst contained approximately 3% by weight palladium.

After drying completely at 125° C., the catalyst was then calcined at 300° C. for 3 hours. The catalyst was then cooled, mixed with glass beads (volume of catalyst and beads is approximately 40 cc.) and placed in a 40 cc. fixed bed reactor. The catalyst was then heated to 400° C. under a nitrogen stream (approximately 55 cc./min.) for 1 hour. Hydrogen was then added to the nitrogen stream (approximately 250 cc./min.) and heating was continued for another 30 minutes. Finally, the catalyst was heated at 400° C. under a stream of hydrogen (approximately 600 cc./min.) for 1 hour.

Decarbonylation

The above catalyst (10 gms.) was heated to 200° C. under a pressure of 1100 psig and in the presence of a nitrogen stream (760 cc./min.). A mixture of iso and normal butyraldehyde in a molar ratio of 1.39 was pumped into the nitrogen stream ahead of the catalyst bed at a rate of 0.145 cc./min. After 1 hour, gas samples were taken for analysis. The reaction was continued for 117.9 minutes during which the liquid products were collected and cooled in a series of traps while another gas sample was collected. The volume of gas through the system was measured (157.195 l.). The liquid in the traps and the effluent gases were analyzed by gas chromatography. The results from this experiment can be found in Table I.

Example 2

A catalyst comprising 3% palladium on a NaY zeolite was prepared in accordance to the procedure of Example 1 and placed into the identical experimental apparatus. The process conditions utilized and the results obtained are shown in Table I.

Examples 3 through 5

Catalysts comprising 3% palladium on zeolites were prepared in accordance with the procedure of Example 1 except that the NaY zeolite was replaced with 5A, 4A and 3A zeolites, respectively. These catalysts were placed into the same experimental apparatus as above and the process conditions were identical to Example 2. The results are shown in Table I.

Examples 6 and 7

Catalysts comprising 3% palladium on zeolites were prepared in a manner similar to Example 1 except that the metal was exchanged and not impregnated onto the zeolite support. The metal cation exchange proceeded according to the following procedure. Pd-acetate (0.4 gms) was dissolved in 30 ml. of acetone and 10 ml. of water and the Pd-acetate-acetone mixture was contacted with 11 gms. of NaY zeolite for 4 days after which the solution had lost most of its red color and the zeolite appeared red-brown. The zeolite was rinsed with water and contacted with a fresh solution of Pd-acetate, prepared as above, overnight. The zeolite was again rinsed with water, dried at 125° C. and calcined at 300° C. for 3 hours. The Pd exchanged molecular sieve 5A catalyst was prepared in similar fashion. These catalysts were placed in the same experimental apparatus as above under the same process conditions as Example 2. The results are shown in Table I.

Example 8

A catalyst comprising 3% palladium on a silica support was prepared in accordance with the procedure of Example 1. The silica gel pellets were about 1/16 of an inch in length, had a surface area of approximately 80 m²/g and were purchased from Calsicat (49B-096B). The experimental apparatus was the same as in Example 1 and the process conditions and results of this experiment are reported in Table I.

Example A

A catalysts comprising 3% palladium on an alumina support was prepared in accordance with the procedure of Example 1. The alumina support was activated alumina in the form of ⅛ inch tablets purchased from MCB Manufacturing Chemists, Inc. The experimental apparatus was the same as in Example 1 and the process conditions and results of this experiment are reported in Table I.

Example A exhibited a lower ratio of propylene/propane, which is undesirable for recycling propylene to butyraldehyde, and a lower selectivity than Examples 1 to 7.

Example B

In this example, the commercially prepared NaY zeolite was used in the experimental apparatus of Example 1. No metal was exchanged or impregnated on the zeolite in this experiment and the results are found in Table I.

Example B produced high yields of dimers and trimers of the aldehyde which are again undesirable for recycling to the hydroformylation reaction.

TABLE I

| | | | Decarbonylation of Butyraldehydes to Propylene | | | | |
| | | | Iso-BA/n-BA | | | | Propylene/ |
| Example[1] | Catalyst | Method of Preparation | In | Out | % Conver.[2] | % Select. | Propane |
| --- | --- | --- | --- | --- | --- | --- | --- |
| 1 | Pd NaY | Impregnated | 1.39 | 1.62 | 41.8 | 44.2 | 0.5 |
| 2 | Pd NaY | Impregnated | 1.00 | 1.94 | 41.2 | 72.9 | 5.0 |
| 3 | Pd 5A | Impregnated | 0.99 | 1.38 | 46.0 | 59.6 | 3.0 |
| 4 | Pd 4A | Impregnated | 0.98 | 1.44 | 45.9 | 61.4 | 5.9 |
| 5 | Pd 3A | Impregnated | 0.99 | 1.38 | 41.5 | 60.5 | 8.3 |
| 6 | Pd NaY | Exchanged | 1.00 | 2.38 | 56.0 | 66.0 | 2.0 |
| 7 | Pd 5A | Exchanged | 1.00 | 1.44 | 46.6 | 60.4 | 3.7 |
| 8 | Pd silica pellets | Impregnated | 0.99 | 1.87 | 38.6 | 62.3 | 7.4 |
| A | Pd alumina | Impregnated | 0.99 | 1.67 | 67.7 | 56.2 | 1.0 |
| B | NaY | — | 0.72 | 2.74 | 33.0* | — | — |

[1] Experiments 2–7, A and B were run at atmospheric pressure while Experiment 1 was run at 1100 psig. All experiments were conducted at 200° C.

[2] % Conversion = $\frac{\text{moles of BA reacted}}{\text{moles of BA fed}} \times 100$

[3] % Selectivity = $\frac{\text{moles of n-BA reacted}}{\text{moles of aldehyde reacted}} \times 100$ BA = butyraldehyde
*Conversions to dimers and trimers of aldehydes

Examples 9 through 12

Catalysts were prepared in accordance with the procedure of Example 1 except the palladium was replaced with silver, copper, zinc and gold, respectively. These metals were added in the form of nitrate salts of Ag, Cu and Zn and AuCl for gold, and comprised approximately 3% metal. These catalysts were placed into the experimental apparatus of Example 1 and the results are shown in Table II.

TABLE II

| | | Method of | Iso-BA/n-BA | |
| Example[1] | Catalyst | Preparation | In | Out |
| --- | --- | --- | --- | --- |
| 9 | AgNaY | Impregnation | 1.39 | 2.02 |
| 10 | CuNaY | Impregnation | 1.00 | 1.11 |
| 11 | ZnNaY | Impregnation | 1.25 | 2.30 |
| 12 | AuNaY | Impregnation | 0.83 | 2.15 |

[1] All experiments were conducted at 1100 psig and 200° C.

Examples 1 through 12 demonstrate the high selectivity for decarbonylating the n-aldehyde and for producing olefinic products suitable for recycle. Examples A and B are provided for comparison with the catalyst used in the invention. When palladium is impregnated on an alumina support as in Example A, the catalyst selectivity for n-butyraldehyde decarbonylation is lower than the catalyst comprising palladium supported on zeolites when utilized under the same conditions. The use of the alumina support also results in a high amount of propane production. Although the use of only a NaY zeolite in the decarbonylation reaction (Example B) exhibited a high selectivity for n-butyraldehyde, aldol condensation occurred yielding dimers and trimers of the aldehydes. Since it is an object of this invention to selectively decarbonylate n-aldehydes as well as obtain reactant products which can be recycled for use in a carbonylation reaction, namely olefins, carbon monoxide and hydrogen, the results of examples A and B are unacceptable.

Thus, it should be apparent to those skilled in the art that the subject invention accomplishes the objects set forth above. It is to be understood that the subject invention is not limited by the examples set forth herein which have been provided merely to demonstrate operability. The selection of catalyst component containing compounds, catalyst formulations, aldehyde ratios and reaction conditions can be determined from the total specification disclosure provided without departing from the spirit of the invention herein disclosed and described. The scope of this invention includes equivalent embodiments, modifications and variations that fall within the scope of the attached claims.

What is claimed is:

1. A process for selectively decarbonylating an n-aldehyde from a mixture comprising n-aldehydes and branched aldehydes to an olefin having one less carbon atom than the n-aldehyde, carbon oxide and hydrogen by passing the mixture over a catalyst comprising a metal selected from the group consisting of palladium, platinum, rhodium, copper, silver, gold and zinc, the metal being supported on or exchanged onto a zeolite.

2. The process of claim 1 wherein the metal is selected from the group consisting of copper, silver, gold and zinc.

3. The process of claim 1 wherein the zeolite is selected from the group consisting of type "A" and "Y".

4. The process of claim 3 wherein the zeolite is selected from the group consisting of NaY, 5A, 4A and 3A.

5. The process of claim 1 wherein the n-aldehyde has from 4 to 6 carbon atoms.

6. The process of claim 5 wherein the n-aldehyde is n-butyraldehyde.

7. The process of claim 6 wherein the decarbonylation occurs in the vapor phase.

8. A process for selectively decarbonylating an n-aldehyde from a mixture comprising n-aldehydes and branch aldehydes to an olefin having one less carbon atom than the n-aldehyde, carbon monoxide and hydrogen by passing the mixture over a catalyst comprising a metal selected from the group consisting of palladium, platinum, rhodium, copper, silver, gold and zinc, the metal being supported on a silica support.

9. The process of claim 8 wherein the metal is selected from the group consisting of copper, silver, gold and zinc.

10. The process of claim 8 wherein the n-aldehyde has from 4 to 6 carbon atoms.

11. The process of claim 10 wherein the n-aldehyde is n-butyraldehyde.

12. The process of claim 11 wherein the decarbonylation occurs in the vapor phase.

13. A process for selectively decarbonylating an n-aldehyde from a mixture comprising n-aldehydes and branch aldehydes to an olefin having one less carbon atom than the n-aldehyde, carbon monoxide and hydrogen by passing the mixture over a catalyst comprising a metal selected from the group consisting of palladium, platinum, rhodium, copper, silver, gold and zinc, the metal being supported on a silica support.

* * * * *